US010550225B2

(12) United States Patent
Sakai et al.

(10) Patent No.: US 10,550,225 B2
(45) Date of Patent: Feb. 4, 2020

(54) PROCESS FOR PRODUCING LOW-CONCENTRATION GEL USING GEL-PRECURSOR CLUSTERS, AND GEL OBTAINED BY SAID PRODUCTION PROCESS

(71) Applicant: The University of Tokyo, Tokyo (JP)

(72) Inventors: Takamasa Sakai, Tokyo (JP); Yuichi Tei, Tokyo (JP)

(73) Assignee: The University of Tokyo, Tokyo (JP)

( * ) Notice: Subject to any disclaimer, the term of this patent is extended or adjusted under 35 U.S.C. 154(b) by 88 days.

(21) Appl. No.: 15/551,442

(22) PCT Filed: Mar. 3, 2016

(86) PCT No.: PCT/JP2016/056522
§ 371 (c)(1),
(2) Date: Aug. 16, 2017

(87) PCT Pub. No.: WO2016/143647
PCT Pub. Date: Sep. 15, 2016

(65) Prior Publication Data
US 2018/0030205 A1   Feb. 1, 2018

(30) Foreign Application Priority Data
Mar. 10, 2015  (JP) .................................. 2015-047388

(51) Int. Cl.
*C08G 65/329* (2006.01)
*C08G 65/333* (2006.01)
(Continued)

(52) U.S. Cl.
CPC ........ *C08G 65/33306* (2013.01); *A61L 27/00* (2013.01); *A61L 27/18* (2013.01);
(Continued)

(58) Field of Classification Search
CPC ............................................... C08G 65/33306
See application file for complete search history.

(56) References Cited

U.S. PATENT DOCUMENTS 6,201,065 B1   3/2001 Pathak et al.
6,410,645 B1   6/2002 Pathak et al.
(Continued)

FOREIGN PATENT DOCUMENTS

EP         2397164       12/2011
JP         11-510837      9/1999
(Continued)

OTHER PUBLICATIONS

European Search Report dated Oct. 19, 2018 corresponding to European Patent Application No. 16761617.6; 8 pages.
(Continued)

*Primary Examiner* — Michael F Pepitone
(74) *Attorney, Agent, or Firm* — Leason Ellis LLP

(57) ABSTRACT

[Problem] To provide a gel which can be produced in a short time, has controlled properties such as modulus and expansion pressure, and has a low polymer concentration. [Solution] A process for producing a polymer gel in which gel-precursor clusters have been crosslinked with one another to form a three-dimensional network structure, characterized by comprising a) a step in which monomer or polymer units that are present in a concentration less than a critical gelation concentration are crosslinked to form the gel-precursor clusters, the gel-precursor clusters having a storage modulus G' and a loss modulus G" which satisfy the relationship G'<G", and b) a step in which the gel-precursor clusters are crosslinked with one another by a crosslinking agent to obtain a gel having a three-dimensional network structure.

23 Claims, 8 Drawing Sheets

(51) Int. Cl.
  *A61L 27/00* (2006.01)
  *A61L 27/18* (2006.01)
  *A61L 27/52* (2006.01)
  *C08J 3/075* (2006.01)
  *C08J 3/24* (2006.01)

(52) U.S. Cl.
  CPC ............ *A61L 27/52* (2013.01); *C08G 65/333* (2013.01); *C08G 65/33337* (2013.01); *C08J 3/075* (2013.01); *C08J 3/244* (2013.01); *C08J 3/246* (2013.01); *A61L 2430/16* (2013.01); *C08G 2210/00* (2013.01); *C08J 2300/10* (2013.01); *C08J 2300/105* (2013.01); *C08J 2300/106* (2013.01); *C08J 2300/14* (2013.01); *C08J 2333/12* (2013.01); *C08J 2371/02* (2013.01); *C08J 2400/10* (2013.01); *C08J 2400/105* (2013.01); *C08J 2400/106* (2013.01); *C08J 2433/12* (2013.01); *C08J 2471/02* (2013.01)

(56) References Cited

U.S. PATENT DOCUMENTS

| | | |
|---|---|---|
| 2002/0151650 A1 | 10/2002 | Pathak et al. |
| 2004/0072961 A1 | 4/2004 | Pathak et al. |
| 2005/0238722 A1 | 10/2005 | Pathak et al. |
| 2008/0187568 A1 | 8/2008 | Sawhney |
| 2010/0100123 A1 | 4/2010 | Bennett |
| 2011/0045047 A1 | 2/2011 | Bennett et al. |
| 2011/0293687 A1 | 12/2011 | Bennett |
| 2011/0293688 A1 | 12/2011 | Bennett |
| 2011/0293692 A1 | 12/2011 | Bennett |
| 2011/0293699 A1 | 12/2011 | Bennett |
| 2012/0049689 A1 | 3/2012 | Bennett |
| 2012/0064299 A1 | 3/2012 | Bennett |
| 2012/0122949 A1* | 5/2012 | Tei ............... C08G 65/3324 514/422 |
| 2014/0228453 A1 | 8/2014 | Bennett |

FOREIGN PATENT DOCUMENTS

| | | |
|---|---|---|
| JP | 2011510837 | 9/1999 |
| JP | 2006097031 | 4/2006 |
| JP | 2007111300 | 5/2007 |
| JP | 2010094519 | 4/2010 |
| JP | 2010519183 | 6/2010 |
| JP | 2011245311 | 12/2011 |
| JP | 2011245312 | 12/2011 |
| JP | 2011246712 | 12/2011 |
| JP | 2011246713 | 12/2011 |
| JP | 2011246714 | 12/2011 |
| JP | 2012096038 | 5/2012 |
| JP | 2015137430 | 7/2015 |
| WO | 200062827 | 10/2000 |
| WO | 200064977 | 11/2000 |
| WO | 2007083522 | 7/2007 |
| WO | 2010070775 | 6/2010 |
| WO | 2012035598 | 3/2012 |

OTHER PUBLICATIONS

Lihui Weng et al. "Rheological Characterization of in situ Crosslinkable Hydrogels Formulated from Oxidized Dextran and N-Carboxyethyl Chitosan" Biomacromolecules. 2007, 8(4): 1109-1115.
Written Opinion dated May 31, 2016 corresponding to International Patent Application No. PCT/JP2016/056522; 12 pages.
International Search Report dated May 31, 2016 corresponding to International Patent Application No. PCT/JP2016/056522; 5 pages.
Takamasa Sakai, et al., Macromolecules, 41, 5379-5384,2008.
Manami Kurakazu, et al., Macromolecules, 43, 3935-3940,2010.
Hiroyuki Kamata, et al., Science, 343, 873-875, 2014.

* cited by examiner a) Formation of gel precursor clusters b) Formation of polymer gel

PROCESS FOR PRODUCING LOW-CONCENTRATION GEL USING GEL-PRECURSOR CLUSTERS, AND GEL OBTAINED BY SAID PRODUCTION PROCESS

CROSS-REFERENCE TO RELATED APPLICATIONS

This application is a 371 national stage application of International Application No. PCT/JP2016/056522 filed on Mar. 3, 2016, which claims priority to JP 2015-047388 filed on Mar. 10, 2015.

TECHNICAL FIELD

The present invention relates to a novel polymer hydrogel.

BACKGROUND ART

Polymer gels that have a network structure have excellent properties such as water retention capacity and biocompatibility, for which reason there has been a focus on studies in which such gels are embedded in vivo as artificial tissues, materials for regeneration scaffolds, and the like (Non-patent Reference 1). A problem, however, has been that polymer gels cause compressive damage in the tissues surrounding the region in which they are embedded because of the osmotic pressure generated from the difference in concentration between the inside of the gel and the outer environment in water. Furthermore, the decomposition of polymer gels elevates the expansion pressure.

Such expansion pressure is proportional to the square of the polymer concentration constituting the gel, and therefore the effects of expansion become more prominent when the polymer concentration is high. Lowering the concentration of the polymer is an essential solution since crosslinks break by changes over time even if the degree of cross linking is raised to lower the expansion ratio. However, it has been difficult to produce a gel in a short time by conventional polymer gel production processes when the polymer concentration is lowered to a level at which expansion does not create tissue damage. It has also been difficult to control the physical properties since physical properties such as the modulus of elasticity change dramatically when the polymer concentration is low and a gel is formed in regions in the vicinity of the gelation points.

PRIOR ART REFERENCES

Non-Patent References

Non-patent Reference 1: Sakai, et. al.: Macromolecules, 41, 5379-5384, 2008
Non-patent Reference 2: Kurakazu, et al.: Macromolecules, 43, 3935-3940, 2010
Non-patent Reference 3: Kamata, et al.: Science, 343, 873-875, 2014

SUMMARY OF THE INVENTION

Problems to be Solved by the Invention

The purpose of the present invention is to develop a gel with which the problem of tissue damage due to expansion when embedded in vivo can be circumvented and a process for the production thereof, and to provide a gel having a low-concentration polymer content that can be produced in a short time and has controlled properties such as modulus of elasticity and expansion pressure.

Means Used to Solve the Above-mentioned Problems

The inventors discovered, as a result of in-depth studies, that, by forming gel precursor clusters in a state on the verge of gelation; i.e., in a state in which the storage modulus $G'$ is lower than the loss modulus $G''$, and using such clusters as a precursor of the subsequent gelation reaction, the gel precursor clusters act as very readily gelled polymer units and make it possible to obtain a gel with a low polymer concentration having controlled properties in a short time.

Specifically, according to the present invention of a first aspect there is provided (1) a process for producing a polymer gel that forms a three-dimensional network structure by crosslinking of gel precursor clusters with one another, wherein the process if characterized by comprising a) a step in which monomer units or polymer units that are present in a concentration less than a critical gelation concentration are crosslinked to form the gel precursor clusters, the gel precursor clusters having a storage modulus $G'$ and a loss modulus $G''$ which satisfy the relationship $G'<G''$, and b) a step in which the gel precursor clusters are crosslinked with one another with a crosslinking agent to obtain a gel having a three-dimensional network structure.

According to preferred modes of the process of the present invention there are provided:

2) the process according to (1) above wherein the loss modulus $G''$ is in a range of 0.005-5 Pa at a frequency of 1 Hz;

(3) the process according to (1) or (2) above wherein the gel precursor clusters have a fractal dimension of 1.5-2.5;

(4) the process according to any of (1)-(3) above wherein the gel precursor clusters having a diameter in a range of 10-1000 nm;

(5) the process according to any of (1)-(4) above wherein the gel has a polymer content of 50 g/L or less;

(6) the process according to any of (1)-(5) above wherein the monomer unit has a vinyl skeleton or the polymer unit has a polyethylene glycol skeleton or a polyvinyl skeleton;

(7) the process according to any of (1)-(6) above wherein the gel precursor clusters comprise a first polymer unit having one or more nucleophilic functional groups in a side chain or at an end and a second polymer unit having one or more electrophilic functional groups in a side chain or at an end;

(8) the process according to (7) above wherein the nucleophilic functional groups are selected from the group consisting of an amino group, —SH, and —CO$_2$PhNO$_2$, and the electrophilic functional groups are selected form the group consisting of an N-hydroxysuccinimidyl (NHS) group, sulfosuccinimidyl group, maleimidyl group, phthalimidyl group, imidazoyl group, acryloyl group, and nitrophenyl group;

(9) the process according to (7) or (8) above wherein the gel precursor clusters comprise first gel precursor clusters and second gel precursor cluster, the first gel precursor clusters having a higher first polymer unit content than second polymer unit content, and the second gel precursor clusters having a higher second polymer unit content than first polymer unit content;

(10) the process according to any of (1)-(9) above wherein step b) is conducted with a reaction time of within one hour; and

(11) the process according to any of (1)-(10) above wherein the crosslinking agent in step b) is bis(sulfosuccinimidyl) glutarate (BS$_2$G), DL-dithiothreitol (DTT), or a synthetic peptide having a thiol group at an end.

According to another aspect, the present invention relates to gel precursor clusters and provides:

(12) gel precursor clusters obtained by cross linking monomer units or polymer units present in a concentration less than a critical gelation concentration wherein the gel precursor clusters contain a solvent and have a storage modulus G' and a loss modulus G" in a relationship of G'<G";

(13) gel precursor clusters according to (12) above wherein the loss modulus G" is in a range of 0.005-5 Pa at a frequency of 1 Hz;

(14) gel precursor clusters according to (12) or (13) above wherein the gel precursor clusters have a fractal dimension of 1.5-2.5;

(15) gel precursor clusters according to any of (12)-(14) above wherein the gel precursor clusters have a diameter in a range of 10-1000 nm;

(16) gel precursor clusters according to any of (12)-(15) above wherein the monomer unit has a vinyl skeleton or the polymer unit has a polyethylene glycol skeleton or a polyvinyl skeleton;

(17) gel precursor clusters according to any of (12)-(16) above comprising a first polymer unit having one or more nucleophilic functional groups in a side chain or at an end and a second polymer unit having one or more electrophilic functional groups in a side chain or at an end; and

(18) gel precursor clusters according to (17) above wherein the nucleophilic functional groups are selected from the group consisting go an amino group —SH, and —Co$_2$PhNO$_2$, and the electrophilic functional groups are selected from the group consisting of an N-hydroxysuccinimidyl (NHS) group, sulfosuccinimidyl group, maleimidyl group, phthalimidyl group, imidazoyl group, acryloyl group, and nitrophenyl group.

According to yet another aspect, the present invention relates to a polymer gel and provides:

(19) a polymer gel obtained by the process according to any of (1)-(11) above;

(20) a polymer gel that forms a three-dimensional network structure by cross linking polymer units with each other wherein the polymer gel contains a solvent, has a polymer content of 50 g/L or less, has a storage modulus G' of 1-10,000 Pa at a frequency of 1 Hz, and has a fractal dimension of 1.5-3.0;

(21) a polymer gel according to (20) above having a loss modulus G" of 1-100 Pa.

(22) a polymer gel according to (20) or (21) above wherein the monomer unit has a vinyl skeleton or the polymer unit has a polyethylene glycol skeleton or a polyvinyl skeleton;

(23) a polymer gel according to any of (20)-(22) above wherein the polymer units comprise a first polymer unit having one or more nucleophilic functional groups in a side chain or at an end and a second polymer unit having one or more electrophilic functional groups in a side chain or at an end;

(24) a polymer gel according to (23) above wherein the nucleophilic functional groups are selected from the group consisting of an amino group, —SH, and —CO$_2$PhNO$_2$, and the electrophilic functional groups are selected from the group consisting of an N-hydroxysuccinimidyl (NHS) group, sulfosuccinimidyl group, maleimidyl group, phthalimidyl group, imidazoyl group, acryloyl group, and nitrophenyl group.

(25) a polymer gel according to any of (20)-(24) above wherein the degree of expansion is such that the change in the volume of the polymer gel in a range of 30-40° C. in an aqueous solution is 90-500% relative to the volume at the time of gel production and the expansion pressure is 0.001-5 kPa; and

(26) a polymer gel according to (25) above wherein the degree of expansion is in a range of 100-200% and the expansion pressure is 0.1-2 kPa.

Advantages of the Invention

By conducting gelation using gel precursor clusters formed in a state artificially on the verge of gelation as a precursor, the present invention makes it possible to produce a gel having a polymer content of a low concentration in a short time while controlling the properties such as the modulus of elasticity and degree of expansion. This allows to provide a gel with which it is able to circumvent the problem of tissue damage due to expansion when embedded in vivo, and the like. This gel can be applied to closed and semi-closed cavities in vivo, such as for artificial vocal cords.

BRIEF DESCRIPTION OF THE DRAWINGS

FIG. 1 is a schematic diagram showing an overview of the production process of the present invention.

FIG. 2 is a graph showing the changes over time in the modulus of elasticity in a common gelation step.

FIG. 3 is a graph showing the changes over time in the modulus of elasticity in step a) of the production process of the present invention.

FIG. 4 is a graph showing the changes over time in the modulus of elasticity in step b) of the production process of the present invention.

FIG. 5 is a graph showing the gelation time in the case of the present invention (△) using gel precursor clusters 1 [TAPEG+TNPEG] and in a comparative example (○).

FIG. 7 is a graph showing the size distribution of gel precursor clusters 1 [TAPEG+TNPEG].

FIG. 8 is a graph showing the results obtained by measuring the dynamic viscosity characteristics at the gelation critical point of gel precursor clusters 1 [TAPEG+TNPEG].

FIG. 9 is a graph showing the fractal dimension of gel precursor clusters 1 [TAPEG+TNPEG].

FIG. 10 is a graph showing the polymer concentration dependence of the modulus of elasticity in polymer gel 1 [TAPEG+TNPEG].

FIG. 11 is a graph showing the polymer concentration dependence of the modulus of elasticity in polymer gel 2 [SHPEG+MAPEG],

FIG. 12 is a photograph showing the changes over time in the expansion of polymer gel 1 [TAPEG+TNPEG] in a semi-closed space,

FIG. 13 is a graph showing the results obtained by measuring the changes over time in the expansion pressure in hydrogel 2 [SHPEG+MAPEG].

BEST MODE FOR CARRYING OUT THE INVENTION

Embodiments of the present invention are explained below. The scope of the present invention is not bound by these explanations, and the present invention can be changed as is appropriate and implemented within the range that does not depart from the spirit of the present invention aside from the following examples.

Figure 1:
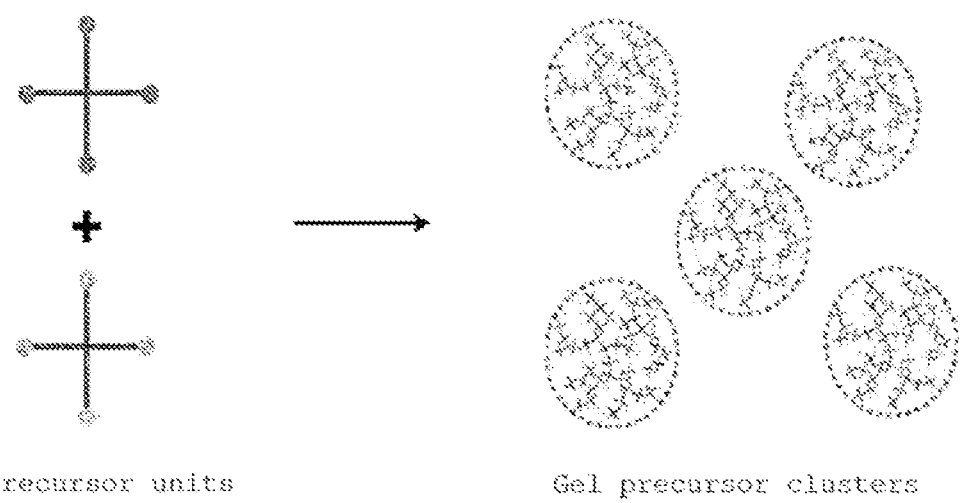
[FIG. 1]
Figure 1:
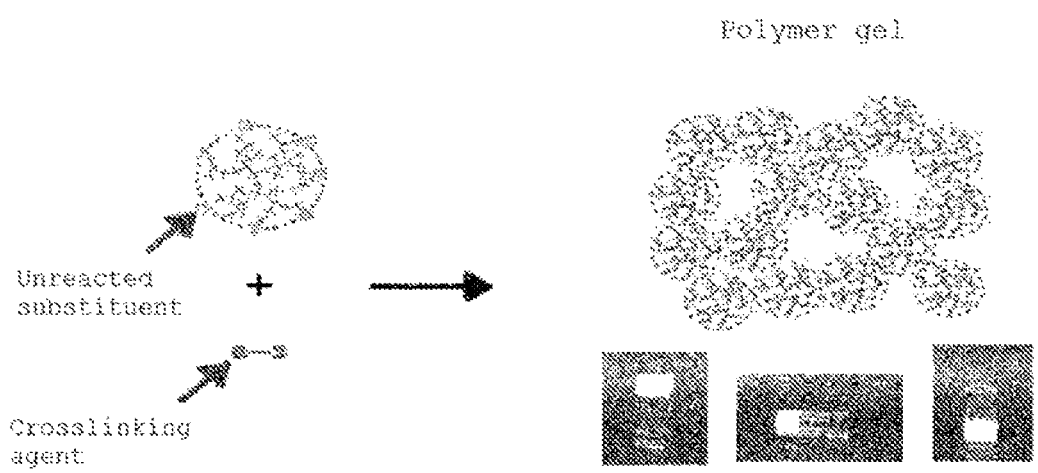

FIG. 1 is a schematic diagram showing a summary of the production process of the present invention. As shown as a first step (FIG. 1a), the monomer units or polymer units (these are referred to as "precursor units" hereinafter) that serve to constitute the polymer gel in the end are reacted in a state on the verge of gelation to have a structure that does not yet form a gel, in other words, to form polymer clusters in a sol state. In addition, as shown as a second step (FIG. 1b), a suitable crosslinking agent is added as a second step, characterized in that these clusters gel precursor clusters are further reacted with each other to obtain a polymer gel, which is the final product, by three-dimensionally crosslinking them with each other. Here, the gel precursor clusters are not necessarily limited to a single type of the same composition, as described below, but multiple gel precursor clusters having different compositions can also be used.

The present invention is based on the novel concept that these gel precursor clusters are used as a precursor or intermediate of the "final gel." A method that makes it possible to form a gel in a short time even in the case of a low-concentration polymer content and to control the modulus of elasticity of the gel even in the low modulus range, which was difficult to do in the prior art, was thereby discovered. Here, "gel" generally refers to a dispersion system that has high viscosity and has lost fluidity.

(1) Gel Precursor Clusters

The gel precursor clusters used in the present invention, as mentioned above, are sol-form polymer clusters obtained by reacting precursor units in a state on the verge of gelation, that is, under conditions below the critical gelation concentration. Here, the "critical gelation concentration" means the minimum concentration of precursor units necessary to achieve gelation in a system that constructs a gel of a three-dimensional structure by crosslinking of specific precursor units. It is also called the minimum gelation concentration. The term critical gelation concentration in the present invention also includes when the concentration of only one type of precursor unit is low, that is, when gelation is not induced due to an inequivalent ratio of each precursor unit, in addition to when the concentrations of all units do not reach the gelation concentration, for example, in a system that uses two or more types of precursor units.

Substituents in an unreacted state are present in the precursor units since these gel precursor clusters are formed under conditions that do not yet attain gelation even though they have a structure in which precursor units are bonded or crosslinked with each other. The final polymer gel having a three-dimensional network structure is obtained by forming further crosslinking of these substituents to each other in the reaction between gel precursor clusters.

Figure 2:
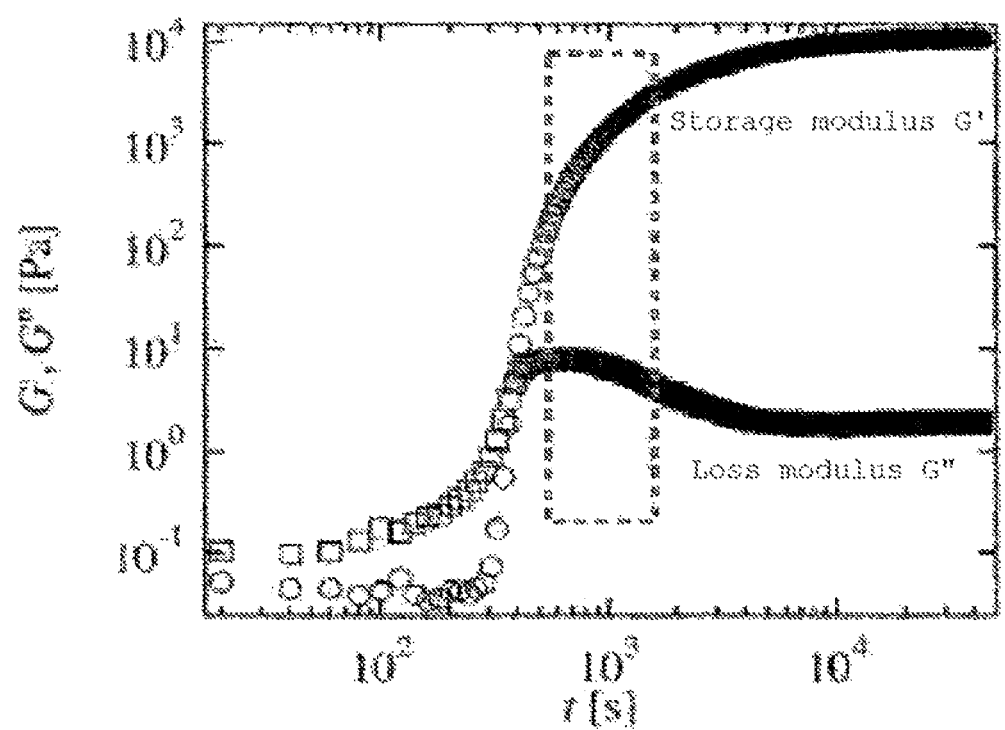
[FIG. 2]

These gel precursor clusters have a relationship of $G'<G''$ between the storage modulus $G'$ and the loss modulus $G''$. As shown in FIG. 2, the value of the loss modulus $G''$ is known to generally be higher than the storage modulus $G'$ in a polymer prior to gelation, and magnitude of these property values reverses, with $G'$ becoming higher, as gelation occurs thereafter. Thus, the point at which $G'=G''$ is the so-called gelation point. Therefore, the fact that $G'<G''$ in the gel precursor clusters means that they are in a sol state, a state that has not yet gelled. Preferably, $G'<G''<100\,G'$ at a frequency of 1 Hz.

Preferably, $G''$ of the gel precursor clusters is in a range of 0.005-5 Pa at a frequency of 1 Hz, more preferably 0.01-1 Pa, and even more preferably 0.01-0.5 Pa. These moduli of elasticity can be calculated by known methods such as dynamic viscosity measurement using a known measurement instrument such as a rheometer.

In addition, the gel precursor clusters in the present invention preferably have a fractal dimension of 1.2-2.5, more preferably a fractal dimension of 1.5-2.0. Here, the fractal dimension is an index representing how close the crosslinked structure formed by the polymer units is to a three-dimensional structure. For the calculation method, reference can be made, for example, to W. Hess, T. A. Vilgis, and H. H. Winter, Macromolecules 21, 2536 (1988). Specifically, the fractal dimension can be calculated, for example, using dynamic scaling theory from the changes in the dynamic viscoelastic characteristics at the gelation point.

The gel precursor clusters in the present invention preferably have a diameter of 10-1000 nm, more preferably 50-200 nm. In addition, the proportion of gel precursor clusters having a diameter of about 100 nm present is preferably greatest in the distribution.

The precursor units used to form the gel precursor clusters can be known ones used in the technical field in accordance with the application, shape, and the like of the final gel as long as they are monomers or polymers capable of forming a gel by a gelation reaction (such as a crosslinking reaction) in a solution. More specifically, polymer units capable of forming a network structure, especially a three-dimensional network structure, by crosslinking of the polymers with each other in the final gel obtained from the gel precursor clusters are preferred.

Examples of monomer units used to form gel precursor clusters are those having a vinyl skeleton. Typical examples of polymer units used to form gel precursor clusters are polymers having a plurality of arms of polyethylene glycol skeletons; polymers having four arms of polyethylene glycol skeletons are especially preferred. Such a gel comprising a four-armed polyethylene glycol skeleton is known as a tetra-PEG gel, and a network-structure network is constructed by an AB-type cross-end coupling reaction between two types of four-armed polymers having an electrophilic functional group such as an active ester structure and a nucleophilic functional group such as an amino group at each end. Based on prior research, tetra-PEG gels are reported to have an ideal homogeneous, network structure with no heterogeneity in the polymer network in the size region of 200 nm and below (Matsunaga, et al., Macromolecules, Vol. 42, No. 4, pp. 1344-1351, 2009). Tetra-PEG gels can also be produced on site easily by simple two-liquid mixing of each polymer solution, and the gelation time can also be controlled by adjusting the pH and ionic strength during gel preparation. These gels also have excellent biocompatibility since the main component is PEG.

However, polymers having other than a polyethylene glycol skeleton can also be used as long as they are capable of forming a network-structure network by crosslinking with each other. For example, polymers having a polyvinyl skeleton such as methyl methacrylate can also be used.

Although not necessarily limited thereto, a means for crosslinking by reacting two types of polymers: a first polymer unit having one or more nucleophilic functional groups in a side chain or at an end and a second polymer unit having one or more electrophilic functional groups in a side chain or at an end, as polymer units for forming gel precursor clusters is suitable for forming a network-structure network in the final gel. Here, the total of nucleophilic functional groups and electrophilic functional groups is preferably five or higher. These functional groups are also preferably present at the ends. The gel precursor clusters can have a composition in which the content of the first polymer units is greater than the content of the second polymer units, or a composition in which the content of the second polymer units is greater than the content of the first polymer units, described below, in a preferred embodiment, a polymer gel can be obtained by crosslinking two or more types of gel precursor clusters of such different compositions.

Examples of nucleophilic functional groups present in the polymer units include an amino group, —SH, or —$CO_2PhNO_2$ (Ph represents an o-, m-, or p-phenylene group), and those skilled in the art can appropriately use known nucleophilic functional groups. Preferably, the nucleophilic functional groups are —SH groups. The nucleophilic functional groups may each be the same or different, but are preferably the same. Having the functional groups be the same makes the reactivity with the electrophilic functional groups that serve to form the crosslinking bonds uniform and makes it easy to obtain a gel having a uniform three-dimensional structure.

Active ester groups can be used as the electrophilic functional groups present in the polymer units. Examples of such active ester groups include an N-hydroxy-succinimidyl (NHS) group, sulfosuccinimidyl group, maleimidyl group, phthalimidyl group, imidazoyl group, acryloyl group, and nitrophenyl group, and those skilled in the art can appropriately use known active ester groups. Preferably, the electrophilic functional groups are maleimidyl groups. The electrophilic functional groups may each be the same or different, but are preferably the same. Having the functional groups be the same makes the reactivity with the nucleophilic functional groups that serve to form the crosslinking bonds uniform and makes it easy to obtain a gel having a uniform three-dimensional structure.

Compounds represented by the following formula (I) having four polyethylene glycol skeleton arms and amino groups at the ends can be given as nonlimiting concrete examples preferred as polymer units having nucleophilic functional groups at the ends.

[Chemical formula 1]

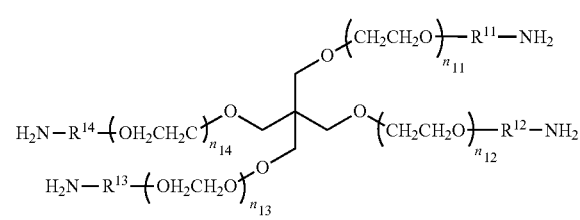

(1)

In formula (I), $R^{11}$-$R^{14}$ are each the same or different and represent a $C_1$-$C_7$ alkylene group, $C_2$-$C_7$ alkenylene group, —NH—$R^{15}$—, —CO—$R^{15}$—, —$R^{16}$-$R^{17}$, —$R^{16}$—NH—$R^{17}$—, —$R^{16}$—$CO_2$—$R^{17}$—, —$R^{16}$—$CO_2$—NH—$R^{17}$—, —$R^{16}$—CO—$R^{17}$—, or —$R^{16}$—CO—NH—$R^{17}$—; here, $R^{15}$ represents a $C_1$-$C_7$ alkylene group, $R^{16}$ represents a $C_1$-$C_3$ alkylene group, and $R^{17}$ represents a $C_1$-$C_5$ alkylene group.)

$n_{11}$-$n_{14}$ may each be the same or different. The closer the values of $n_{11}$-$n_{14}$, the more uniform the three-dimensional structure becomes, and the higher the strength becomes. Therefore, they are preferably the same to obtain a high-strength gel. The gel strength weakens as the values of $n_{11}$-$n_{14}$ become higher, and a gel is difficult to form due to the steric hindrance of the compounds when the values of $n_{11}$-$n_{14}$ are too low. Therefore, $n_{11}$-$n_{14}$ can be integer values of 25-250, preferably 35-180, more preferably 50-115, and especially 50-60. The molecular weight can be $5\times10^3$ to $5\times10^4$ Da, preferably $7.5\times10^3$ to $3\times10^4$ Da, and more preferably $1\times10^4$ to $2\times10^4$ Da.

In the above formula (I), $R^{11}$-$R^{14}$ are linker sites connecting a functional group and the core moiety. $R^{11}$-$R^{14}$ may each be the same or different, but are preferably the same to produce a high-strength gel having uniform three-dimensional structure. $R^{11}$-$R^{14}$ represent a $C_1$-$C_7$ alkylene group, $C_2$-$C_7$ alkenylene group, —NH—$R^{15}$—, —CO—$R^{15}$—, —$R^{16}$—O—$R^{17}$—, —$R^{16}$—NH—$R^{17}$—, —$R^{16}$—$CO_2$—$R^{17}$—, —$R^{16}$—$CO_2$—NH—$R^{17}$—, —$R^{16}$—CO—$R^{17}$—, or —$R^{16}$—CO—NH—$R^{17}$—, Here, $R^{15}$ represents a $C_1$-$C_7$ alkylene group, $R^{16}$ represents a $C_1$-$C_3$ alkylene group and $R^{17}$ represents a $C_1$-$C_5$ alkylene group.

Here, a "$C_1$-$C_7$ alkylene group" means an optionally branched alkylene group having from one to seven carbon atoms, and means a linear $C_1$-$C_7$ alkylene group or a $C_2$-$C_7$ alkylene group having one or more branches (the number of carbon atoms, including the branches, is from two to seven). Examples of $C_1$-$C_7$ alkylene groups are a methylene group, ethylene group, propylene group, and butylene group. Examples of $C_1$-$C_7$ alkylene groups include —$CH_2$—, —$(CH_2)_2$—, —$(CH_2)_3$—, —$CH(CH_3)$—, —$(CH_2)_3$—, —$(CH(CH_3))_2$—, —$(CH_2)_2$—$CH(CH_3)$—, —$(CH_2)_3$—$CH(CH_3)$—, —$(CH_2)_2$—$CH(C_2H_5)$—, —$(CH_2)_6$—, —$(CH_2)_2$—$C(C_2H_5)_2$—, —$(CH_2)_3C(CH_3)_2CH_2$—, and the like.

A "$C_2$-$C_7$ alkenylene group" is a linear or branched, alkenylene group having 2-7 carbon atoms having one or more double bonds in the chain. Examples include divalent groups having double bonds formed by eliminating 2-5 hydrogen atoms of adjacent carbon atoms from an alkylene group.

On the other hand, compounds represented by the following formula (II) having four polyethylene glycol skeleton arms and N-hydroxysuccinimidyl (NHS) groups at the ends can be given as nonlimiting concrete examples preferred as polymer units having electrophilic functional groups at the ends.

[Chemical formula 2]

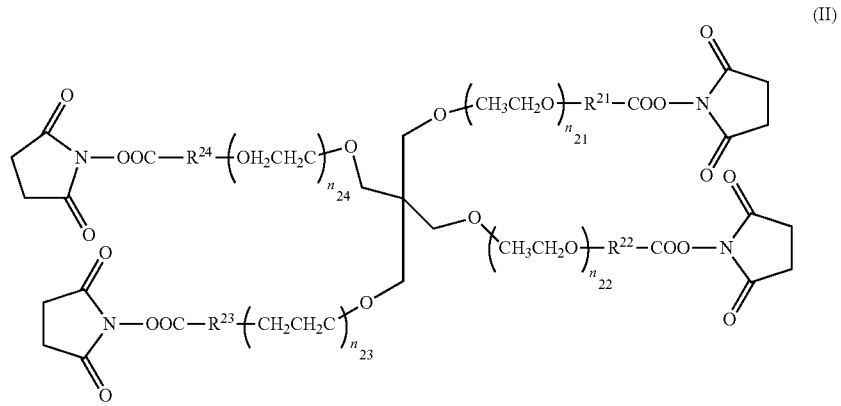

(II)

In the above formula (II), $n_{21}$-$n_{24}$ may each be the same or different. The closer the values of $n_{21}$-$n_{24}$, the more uniform the three-dimensional structure becomes, and the higher the strength becomes. Therefore, they are preferably the same. The gel strength weakens as the values of $n_{21}$-$n_{24}$ become higher, and a gel is difficult to form due to the steric hindrance of the compounds when the values of $n_{21}$-$n_{24}$ are too low. Therefore, $n_{21}$-$n_{24}$ can be integer values of 5-300, preferably 20-250, more preferably 30-180, even more preferably 45-115, and especially 45-55. The molecular weight of the second four-armed compound of the present invention can be $5 \times 10^3$ to $5 \times 10^4$ Da, preferably $7.5 \times 10^3$ to $3 \times 10^4$ Da, and more preferably $1 \times 10^4$ to $2 \times 10^4$ Da.

In the above formula (II), $R^{21}$-$R^{24}$ are linker sites connecting a functional group and the core moiety. $R^{21}$-$R^{24}$ may each be the same or different, but are preferably the same to produce a high-strength gel having a uniform three-dimensional structure. In formula (II), $R^{21}$-$R^{24}$ represent a $C_1$-$C_7$ alkylene group, $C_2$-$C_7$ alkenylene group, —NH—$R^{25}$—, —CO—$R^{25}$—, —$R^{26}$—O—$R^{27}$—, —$R^{26}$—NH—$R^{27}$—, —$R^{26}$—$CO_2$—$R^{27}$—, —$R^{26}$—$CO_2$—NH—$R^{27}$—, —$R^{26}$—CO—$R^{27}$—, or —$R^{26}$—CO—NH—$R^{27}$—, Here, $R^{25}$ represents a $C_1$-$C_7$ alkylene group, $R^{26}$ represents a $C_1$-$C_3$ alkylene group. $R^{27}$ represents a $C_1$-$C_5$ alkylene group.

In the present specification, alkylene groups and alkenylene groups may have one or more optional substituents. Examples of said substituents include, but are not limited to, alkoxy groups, halogen atoms (may be any of a fluorine atom, chlorine atom, bromine atom, or iodine atom), amino groups, mono- or di-substituted amino groups, substituted silyl groups, acyl groups, aryl groups, or the like. When an alkyl group has two or more substituents, they may be the same or different. The same is also true of alkyl moieties of other substituents (for example, alkyloxy groups and aralkyl groups) including alkyl moieties.

In addition, in the present specification, when certain functional groups are defined as "optionally substituted," the types of substituents, positions substituted, and number of substituents are not particularly limited, and when they have two or more substituents, the substituents may be the same or different. Examples of substituents include, but are not limited to, alkyl groups, alkoxy groups, hydroxyl groups, carboxyl groups, halogen atoms, sulfo groups, amino groups, alkoxycarbonyl groups, oxo groups, and the like. Other substituents may also be present in these substituents.

In the case of polymer units of the above formula (I) and formula (II), gel precursor clusters of a structure in which the units are linked by amide bonds are obtained. Furthermore, as will be described below, the gel finally obtained in this case also takes on a structure in which each polymer unit is crosslinked by amide bonds.

(2) Gelation Step

An exemplary embodiment of the gelation reaction step in the production process of the present invention comprises:

a) a step that crosslinks monomer units or polymer units (precursor units) present in a concentration less than the critical gelation concentration to form clusters that serve as gel precursors (FIG. 1a), and b) a step that obtains a gel having a three-dimensional network structure, which is the final objective, by crosslinking the gel precursor clusters with one another with a crosslinking agent FIG. 1b).

In step a), as mentioned above, the precursor units are reacted under conditions below the critical gelation concentration by adjusting the starting concentration of precursor units, and a polymer of an ungelled sol state, preferably having a structure on the verge of gelation, is formed. These clusters are referred to as "gel precursor clusters" in this application because they can be called, precursors to the final gel.

When two types of polymer units having nucleophilic functional groups or electrophilic functional groups as described above are used, for example, a low-concentration condition that includes equivalent amounts of these units but overall is not sufficient to achieve gelation is used, or a condition in which the concentration of one type of polymer unit is low, that is, no gel is produced due to inequivalent amounts, is used as the method of adjusting the starting concentrations of precursor units to a condition below the critical gelation concentration.

Generally, the critical gelation concentration (minimum gelation concentration) depends on the types of precursor units used, but such concentrations are known in this technical field or can be ascertained easily by experimentation by those skilled in the art. It is typically 5-50 g/L, with the lower limit being about $\frac{1}{5}$ of the overlapping concentration. Here, the overlapping concentration is the concentration at which polymer units fill the solution. For the calculation method, reference can be made, for example, to Polymer Physics (by M. Rubinstein and R. Colby). Specifically, it can be determined by viscosity measurement of a dilute solution using the Flory-Fox equation.

Step a) typically can be carried out by mixing or applying stimulation to a solution containing two types of precursor units. It can also be carried out by radical polymerization of monomers using a radical polymerization initiator. The concentration of each, solution, addition rate, mixing rate, and mixing ratio are not particularly limited and can be adjusted as appropriate by one skilled in the art. Even when three or more types of precursor units are used, it will be obvious that solutions containing the corresponding precursor units can be prepared and mixed as is appropriate in the same way. Water, alcohols such as ethanol, DMSO, and the like can be used as the solvent of the solution containing the precursor units. If the solution is an aqueous solution, a suitable pH buffer such as phosphate buffer can be used.

A two-solution mixing syringe such as that disclosed, for example, in WO2007/083522 can be used as the mixing means. The temperature of the two solutions during mixing is not particularly limited and should be a temperature that dissolves each of the precursor units and creates a state in which each of the solution is fluid. An example of the solution temperature during mixing is a range of 1° C.-100° C. The temperature of the two solutions may differ, but it is preferable for the ease of mixing the two solutions that the temperature be the same.

Next, in step b), the gel precursor clusters obtained in step a) are further reacted with each other, and a polymer gel, which is the final product, is obtained by three-dimensionally crosslinking them with each other. Since the gel precursor clusters are formed so as to be in a state before the gelation point, as described above, substituents used for crosslinking remain in an reacted state in each of the precursor units. The final gel is formed by crosslinking by reacting these substituents in the gel precursor clusters with residual substituents in other gel precursor clusters.

Preferably, in step b) a crosslinking agent can be added or stimulation applied to crosslink the gel precursor clusters with one another. One having substituents the same as the crosslinking groups in the polymer units can be used as such a crosslinking agent. The polymer units themselves can also be used as a crosslinking agent by adding additional polymer units. For example, when gel precursor clusters were obtained by reacting inequivalent amounts of two types of polymer units having nucleophilic functional groups or electrophilic functional groups in step a), the gel precursor clusters can be crosslinked with precursor clusters were obtained by reacting inequivalent amounts of two types of polymer units having nucleophilic functional groups or electrophilic functional groups in step a), the gel precursor clusters can be crosslinked with each other by adding a crosslinking agent having functional groups of the lower concentration. Bis(sulfosuccinimidyl) glutarate ($BS_2G$), DL-dithiothreitol (DTT), a synthetic peptide having a thiol group at an end, or the like can be used as such a crosslinking agent. In addition, functional groups (maleimide groups, etc.) can be irradiated with ultraviolet light, for example, to cause photodimerization as a stimulation for crosslinking.

Preferably, in step b), the final gel can be obtained by a reaction time of within two hours, preferably a reaction time of within one hour. In contrast to the fact that a long time is generally required as the reaction time (it depends on the system, but, for example, approximately eight hours in the case of a polymer content of 10 g/L or less) when producing a gel containing a polymer in a low concentration, a gel can be produced in a far shorter time in the present invention.

The other reaction solution conditions and the like in step b) are the same as in step a).

(3) Polymer Gel

The polymer gel obtained by the present invention is obtained by a short reaction time, as described above, while having a low concentration polymer content, and makes it possible to control the properties such as the modulus of elasticity within a desired range. As shown in FIG. 2, it was difficult to obtain a gel having a low modulus of elasticity controlled to a specific value within a low modulus of elasticity range of 10-1000 Pa due to a drastic rise in the modulus of elasticity near the gelation point. In contrast to this, the gel of the present invention has a modulus of elasticity controlled in the low modulus of elasticity region because the gel is produced via the gel precursor clusters described above.

The polymer gel of the present invention is therefore a polymer gel forming a three-dimensional network structure by crosslinking of polymer units with each other and is characterized by having a low-concentration polymer content, a modulus of elasticity in the low region, and a specific fractal dimension.

The polymer content in the polymer gel of the present invention is 50 g/L or less, preferably 40 g/L or less, and more preferably 15-30 g/L.

The polymer gel of the present invention has a storage modulus G' of 1-10,000 Pa, preferably 10-1000 Pa. Such a range corresponds to the vitreous body (several 10 Pa) and vocal cords (several 100 Pa) in the living body. In addition, the polymer gel of the present invention preferably has a loss modulus G" of 1-100 Pa. These moduli of elasticity can be calculated by known methods using known measurement instruments.

Furthermore, the polymer gel of the present invention preferably has a fractal dimension of 1.5-2.5. More preferably, it has a fractal dimension of the polymer 1.5-2.0. This fractal dimension is an index representing how close the crosslinked structure formed in the gel is to a three-dimensional structure, and methods of calculating it are known in this technical field, as mentioned above.

The polymer gel of the present invention has an expansion pressure of 0.001-5 kPa, which is a degree of expansion of the range where the volume of the polymer gel in a range of 30-40° C. in an aqueous solution changes 90-500% in volume relative to the volume at the time of gel production. The degree of expansion is preferably in the 100-200% range, and the expansion pressure is preferably 0.1-2 kPa. A low expansion pressure means that the pressure exerted on the outside when the gel is placed in a closed space is low. In other words, this means that tissue damage is low even when the gel absorbs water and swells over time in vivo.

The same ones as are used in the gel precursor clusters mentioned above can be used as the polymer units that constitute the polymer gel of the present invention. In a preferred embodiment, when the gel precursor clusters comprise a first polymer unit having one or more nucleophilic functional groups in a side chain or at an end and a second polymer unit having one or more electrophilic functional groups in a side chain or at an end, two types of gel precursor clusters, a first gel precursor cluster of a composition in which the content of the first polymer units is greater than the content of the second polymer units and a second gel precursor cluster of a composition in which the content of the second polymer units is greater than the content of the first polymer units, can be used as the gel precursor clusters, and a polymer gel of a three-dimensional network structure in which these type types of gel precursor clusters of different compositions are crosslinked with each other can be made.

The polymer gel of the present invention can be processed into a variety of shapes such as a thin film in accordance with the application. Any methods known in this technical field can be used for such processing. For example, in the case of a thin film, a thin film can be obtained by a method such as applying the gel to a flat substrate such as glass in a state of having fluidity prior to complete solidification.

EXAMPLES

The present invention is described in greater detail below through examples. The present invention, however, is in no way limited by these examples.

Example 1

Synthesis of Polymer Units

TAPEG (tetraamine-polyethylene glycol) and TNPEG (N-hydroxy-succinimidyl-polyethylene glycol (NHS-PEG) were obtained by aminating and succinimidylating, respectively, THPEG (tetrahydroxyl-polyethylene glycol) having hydroxyl groups at the ends.

The SHPEG (tetrathiol-polyethylene glycol) having —SH groups at the ends and MAPEG (tetramaleimidyl-polyethylene glycol) having maleimidyl groups at the ends used were each purchased from Nichiyu Corporation. The molecular weight of both is 10,000.

In the following experiment, the $^1$H-NMR spectrum was analyzed using a JEOL JNM-ECS400 (400 MHz). Deuterated chloroform was used as the solvent, and tetramethylsilane served as the internal standard. The molecular weight was determined using the linear positive ion mode of an Ultraflex III mass spectrometer made by Brucker Daltonics, Inc.

1. Synthesis of THPEG:

The initiator pentaerythritol (0.4572 mmol), 62.3 mg) was dissolved in 50 mL of a mixed solvent of DMSO/THF (v/v=3:2). Ethylene oxide (200 mmol, 10.0 mL) was added using potassium naphrene [sic] (0.4157 mmol, 1.24 mg) as a metallizing agent and heated and stirred for approximately two days at 60° C. in the presence of Ar. After the reaction had been completed, the system was reprecipitated by diethyl ether, and the precipitate was removed by filtration. THPEG of 20 k was obtained by washing three times with diethyl ether and drying the white solid obtained under reduced pressure.

2. Synthesis of TAPEG:

THPEG (0.1935 mmol, 3.87 g, 1.0 Eq) was dissolved in benzene, lyophilized, and dissolved in 62 mL of THF, and triethylamine (TEA) (0.1935 mmol, 3.87 g, 1.0 Eq) was added. Thirty-one mL of THF and methanesulfonyl chloride (MsCl) (0.1935 mmol, 3.87 g, 1.0 Eq) were added to a separate eggplant flask and placed in an ice bath. The THF solution of MsCl was added dropwise over approximately one minute to the THF solution of THPEG and TEA, stirred for 30 minutes in an ice bath, then stirred for an hour and a half at room temperature. After the reaction had been completed, the system was reprecipitated with diethyl ether, and the precipitate was removed by filtration. The precipitate was washed three times with diethyl ether, and the white solid obtained was transferred to an eggplant flask where 250 mL of 25% ammonia water was added and stirred for four days. After the reaction had been completed, the solvent was distilled off under reduced pressure by an evaporator, and a white solid of TAPEG was obtained by dialyzing two or three times with water as the outside solution and lyophilizing. Formula (Ia) shows the chemical formula of the TAPEG produced. In formula (Ia), $n_{11}$-$n_{14}$ were 50-60 when the molecular weight of the TAPEG was approximately 10,000 (10 kDa) and 100-115 when the molecular weight was approximately 20,000 (20 kDa).

[Chemical formula 3]

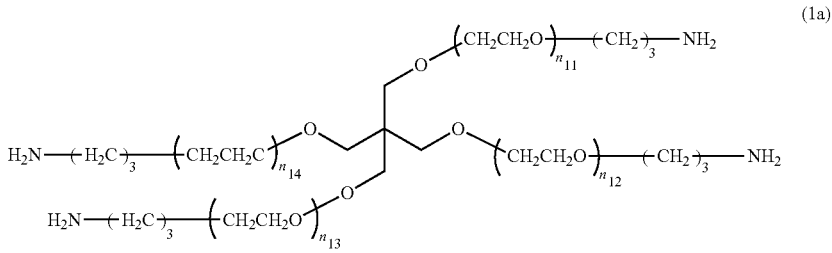

(Ia)

3. Synthesis of TNPEG:

THPEG (0.2395 mmol, 4.79 g, 1.0 Eq) as dissolved in THF, and 0.7 mol/L glutaric acid/THF solution (4.790 mmol, 6.85 mL, 20 Eq) was added, and stirred for six hours in the presence of Ar. After the reaction had been completed, 2-propanol was added dropwise, and the system was centrifuged three times. The white solid obtained was transferred to a 300 mL eggplant flask, and the solvent was distilled off under reduced pressure by an evaporator. The residue was dissolved in benzene, and the insoluble matter was removed by filtration. A white solid of tetra-PEG-COOH having ends modified by carboxyl groups was obtained by removing the solvent by lyophilizing the filtrate obtained. This tetra-PEG-COOH (0.2165 mmol, 4.33 g, 1.0 Eq) was dissolved in THF, N-hydrosuccinamide (2.589 mmol, 0.299 g, 12 Eq) and N,N'-diisopropylsuccinamide (1.732 mmol, 0.269 mL, 8.0 Eq) were added, and heated and stirred for three hours at 40° C. After the reaction had been completed, the solvent was distilled off under reduced pressure by an evaporator. The residue was dissolved in chloroform and extracted three times by saturated saline, and the chloroform layer was removed. After further dehydration by magnesium sulfate and filtration, the solvent was distilled off under reduced pressure by an evaporator. The residue obtained was benzene lyophilized [sic], and a white solid of TNPEG was obtained. Formula (IIa) shows the chemical formula of the TNPEG produced. In formula (IIa), $n_{21}$-$n_{24}$ were 45-55 when the molecular weight of the TNPEG was approximately 10,000 (10 k), and 90-115 when the molecular weight was approximately 20,000 (20 k).

[Chemical formula 4]

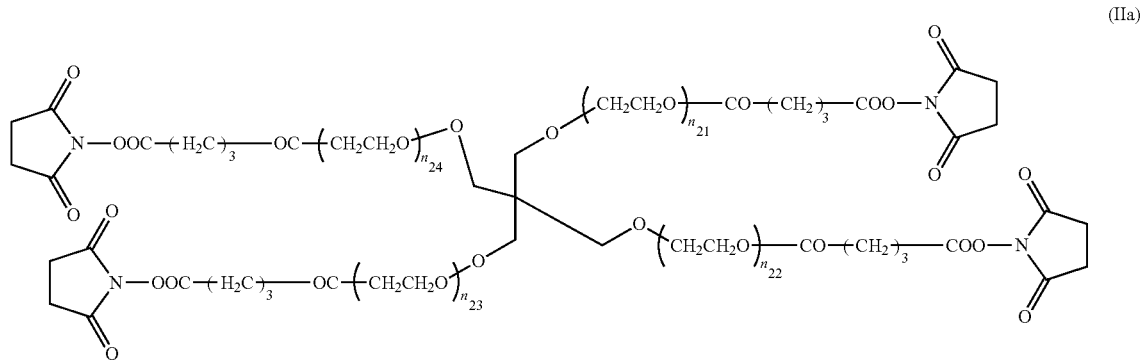

(IIa)

Example 2

Synthesis of Gel Precursor Clusters

Gel precursor clusters, which serve as precursors in the gelation reaction, were synthesized as follows.

(1) Gel Precursor Clusters 1 [TAPEG+TNPEG]

First, the TAPEG ($1.0 \times 10^4$ g/mol) and TNPEG ($1.0 \times 10^4$ g/mol) synthesized in Example 1 were dissolved in the same amounts of 81 mM phosphate buffer and citrate buffer, respectively. The substance ratio at this time was TAPEG/TNPEG=1/0.23, and the total polymer concentration was set at 60 g/L. The two solutions obtained were mixed in a separate container and defoamed and stirred using a planetary centrifugal mixed. Thereafter, the mixed solution was quickly transferred to a Falcon tube, capped to prevent drying, and allowed to stand for 12 hours at room temperature.

Figure 3:
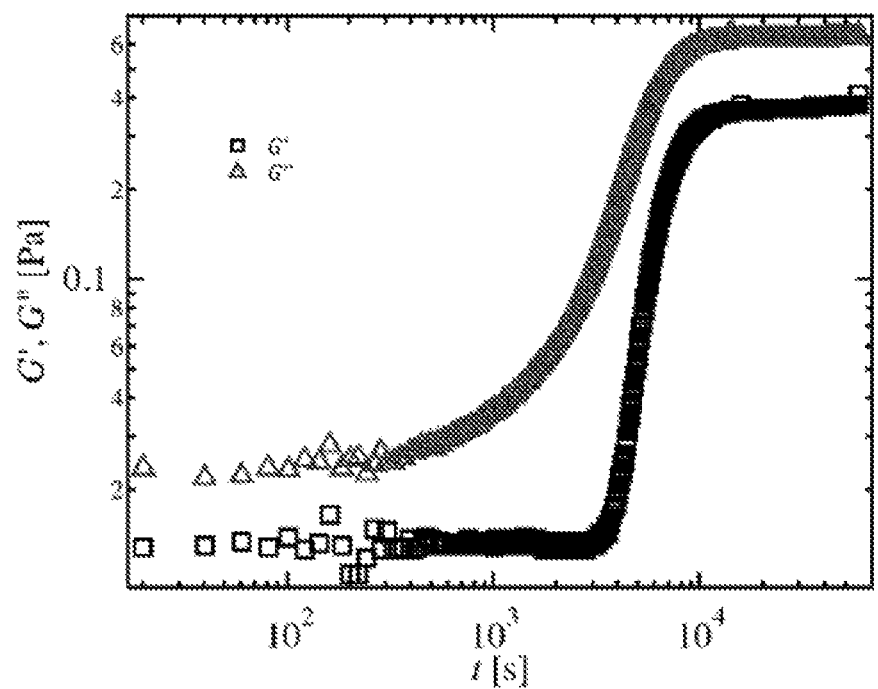
[FIG. 3]

FIG. 3 shows the changes over time in the storage modulus G' and loss modulus G" in this step. The solution had a G'<G" relationship at the end of the reaction, showing that these were polymer clusters in a sol state that had not yet formed a gel.

(2) Gel Precursor Clusters 2 [SHPEG·MAPEG]

Gel precursor clusters 2 were synthesized in the same way using SHPEG and MAPEG. The total polymer concentration was set at 60 g/L. Multiple samples containing the tow types of gel precursor clusters, one of which was contained in an excess to that the molar ratio of SHPEG:MAPEG was (1−r):r, were prepared.

Example 3

Synthesis of Polymer Gel

A polymer gel was synthesized as follows using the gel precursor clusters synthesize din Example 2.

(1) Polymer Gel 1 [TAPEG+TNPEG]

A solution of the gel precursor clusters 1 obtained in Example 2 was diluted by water to 25 g/L. The amount of unreacted amino groups in the solution was calculated, and a crosslinking agent (bis(sulfocussinimidyl) glutarate ($BS_2G$)) was added to make an amount equal thereto, and the system was defoamed and stirred with a planetary centrifugal mixer. Thereafter, the mixed solution was quickly transferred to a Falcon tube, capped to prevent drying, and allowed to stand for 12 hours at room temperature.

Figure 4:
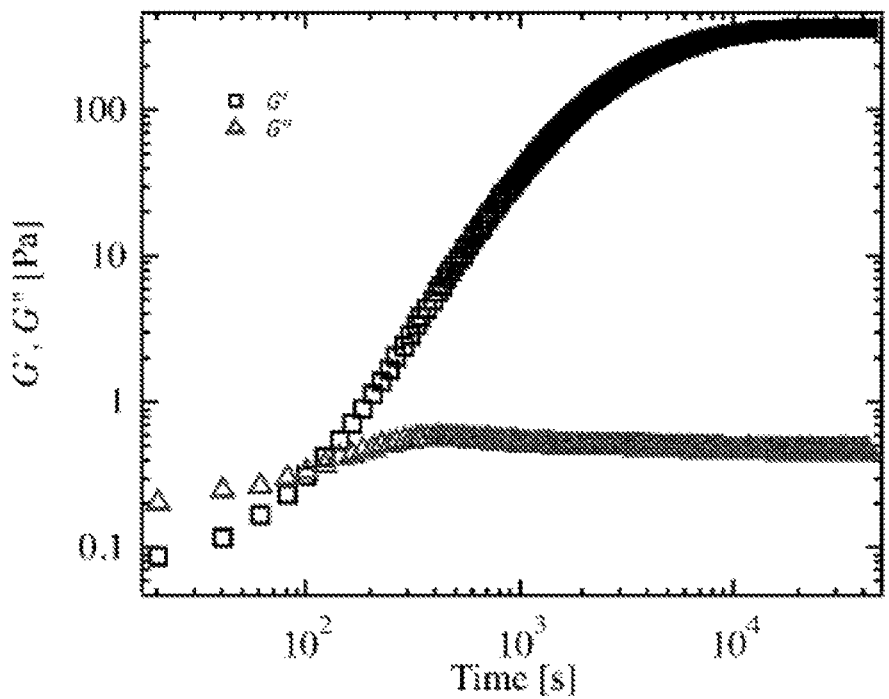
[FIG. 4]

FIG. 4 shows the changes over time in the storage modulus G' and loss modulus G" in this step. The solution had a G'>G" relationship at the end of the reaction, showing that a polymer gel had formed by cross linking of the gel precursor clusters.

Figure 5:
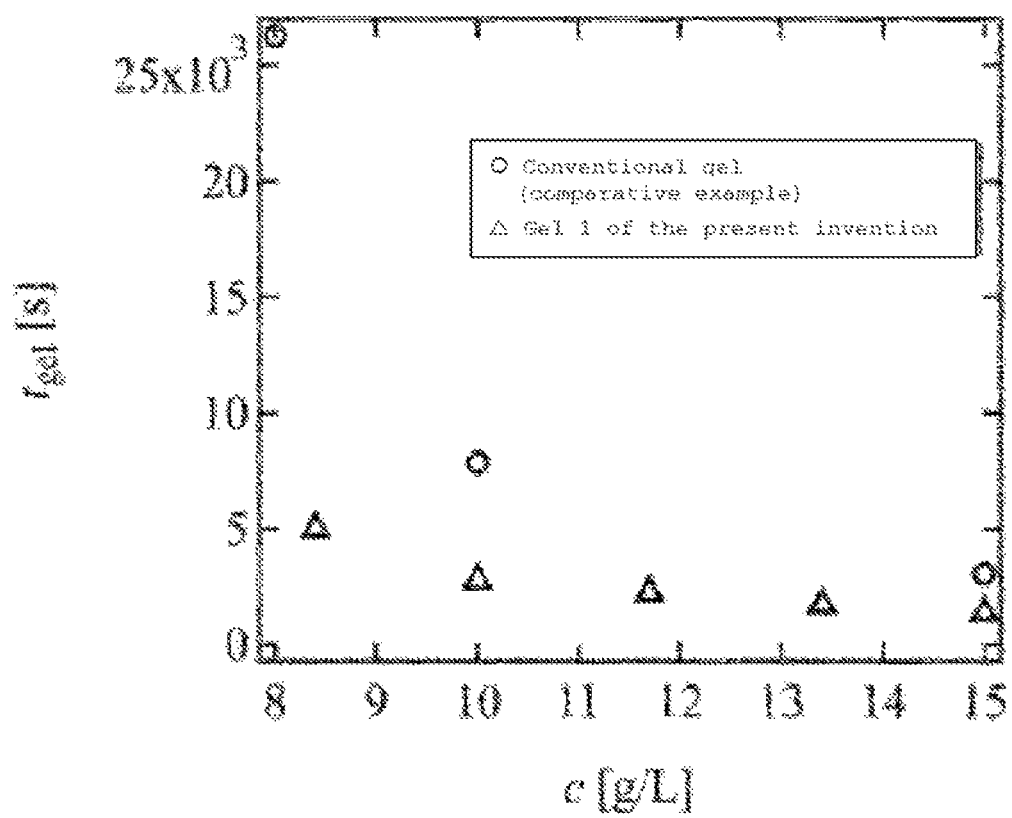
[FIG. 5]

FIG. 5 shows the reaction time when gelation was conducted by varying the concentration of gel precursor clusters. The vertical axis in FIG. 4 is the gelation time $t_{gel}$ (sec), and the horizontal axis is the polymer content c (g/L) in the polymer gel. In the graph, Δ is an example of a polymer gel of the present invention gelled by gel precursor clusters; ○ is a comparative example gelled directly from polymer units by a conventional method without using gel precursor clusters. It is understood as a result that a polymer gel is obtained by a short reaction time when gelled by gel precursor clusters. In particular, gelation occurred within 1.5 hours when the gel precursor clusters of the present invention were used in contrast to the gelation time of seven or more hours required in the case of the conventional method when the polymer content was a low concentration of about 8 g/L. In addition, the gelation time was less than 30 minutes when gel precursor clusters were used in a higher concentration region.

2) Polymer Gel 2 [SHPEG+MAPEG]

Figure 6:
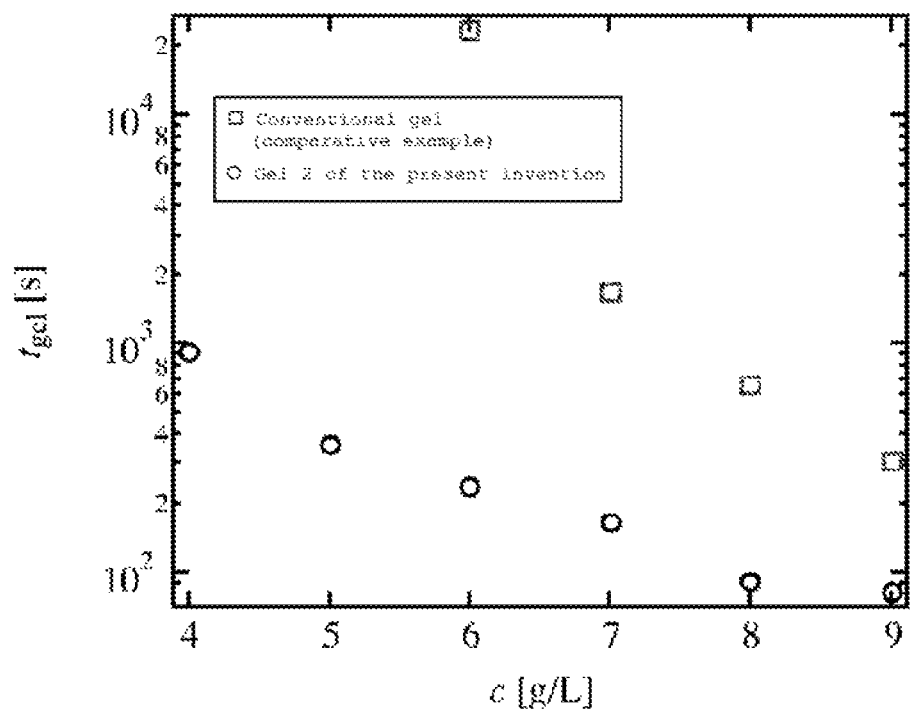
[FIG. 6] FIG. 4 [sic; 6]0 is a graph showing the gelation time in the case of the present invention (○) using gel precursor clusters 2 [SHPEG+MAPEG] and in a comparative example (□).

A polymer gel was produced in the same way using the gel precursor clusters 2 obtained in Example 2. Gel precursor clusters having an excess of SHPEG (10 g/L; r=0.37) and gel precursor clusters having an excess of MAPEG (10 g/L; r=0.63) were each diluted to 6 g/L by citrate buffer containing NaCl, and equal amounts were mixed. In the same way as FIG. 5, FIG. 6 shows the reaction time when gelation was conducted by varying the concentration of gel precursor clusters. In the graph, ○ is an example of a polymer gel of the present invention gelled b y get precursor clusters; □ is a comparative example gelled directly form polymer units by a conventional method without using gel precursor clusters. In particular, gelation occurred in three minutes when the gel precursor clusters of the present invention were used when the polymer content was a low concentration of about 7 g/L. This shows that gel precursor clusters can be injected into the eye during vitreous surgery and gelled in vivo.

Example 4

Properties of Gel Precursor Clusters

1. Size of Gel Precursor Clusters

Figure 7:
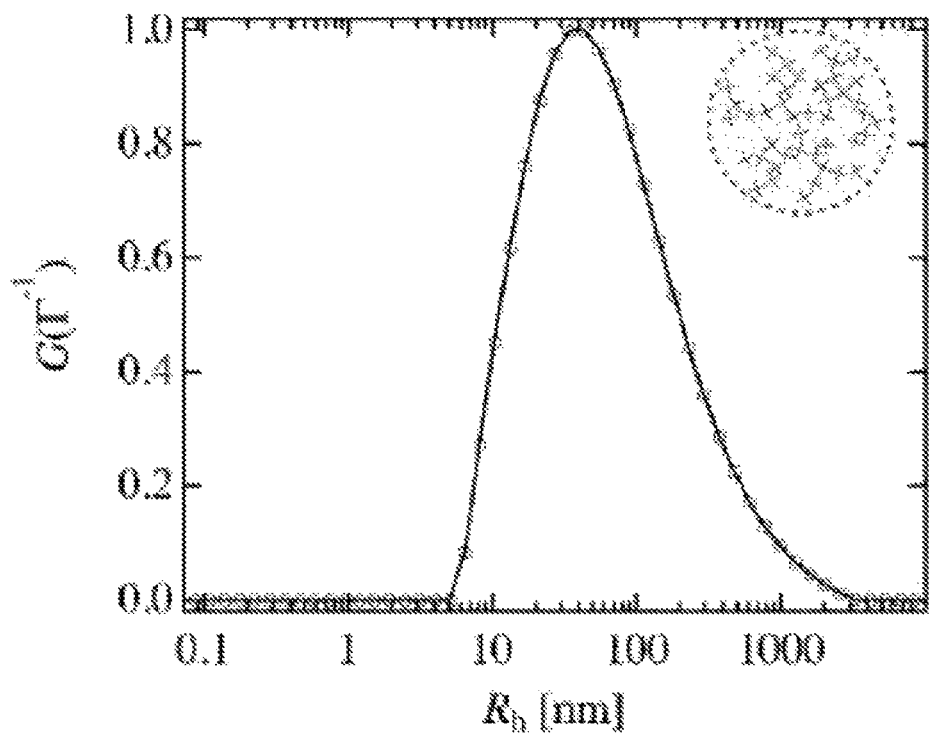
[FIG. 7]

FIG. 7 shows the results obtained by measuring the size distribution of the gel precursor clusters 1 synthesized in Example 2. The horizontal axis Rh is the particle diameter (nm) of the gel precursor clusters, and the vertical axis $G(\lceil^{-1})$ is the characteristic relaxation time distribution function. It was understood as a result that the particle diameter of the gel precursor clusters is several hundred nm, and that most are about 1000 nm. Basically the same results were also obtained for the gel precursor clusters 2 synthesized in Example 2.

2. Modulus of Elasticity

The dynamic viscoelasticity of the gel precursor clusters 1 in solution was measured using a rheometer (Physica MCR501, manufactured by Anton Paar), and the storage modulus G' and loss modulus G" were calculated. As a result G" at 1 Hz was in the range of 0.1<G"<100 Pa, and G'<G"<100 G". This confirmed the gel precursor clusters obtained in Example 2 to be structures that had not reached gelation criticality, as was also shown in FIG. 3 above. Basically the same results were also obtained for the gel precursor clusters 2 synthesized in Example 2.

3. Fractal Dimension

Figure 8:
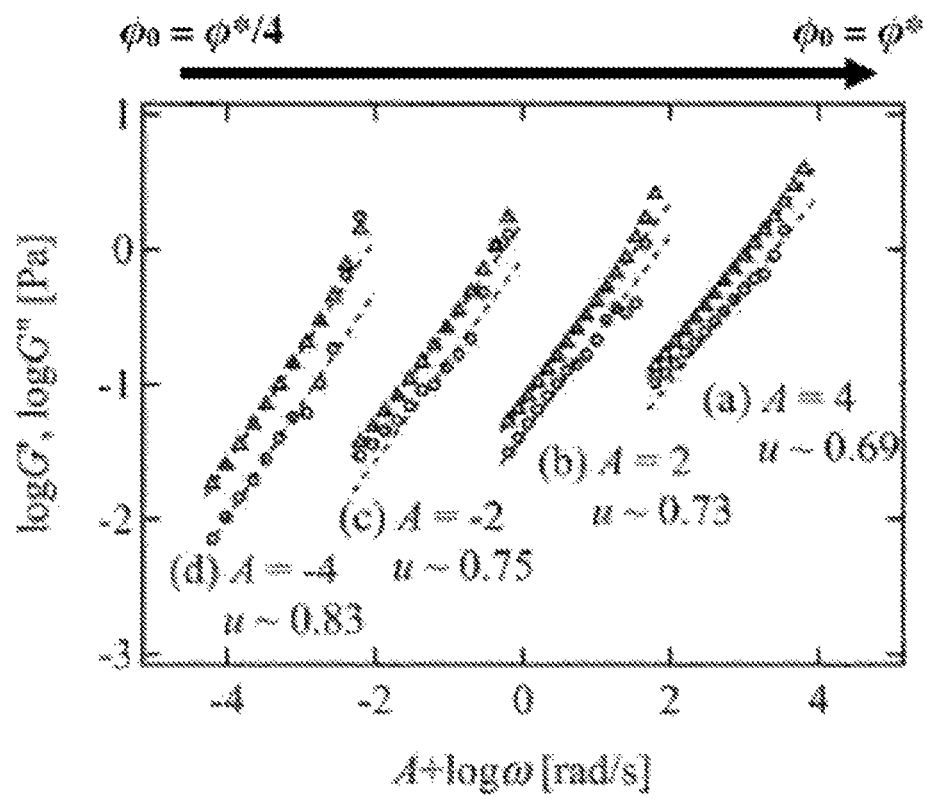
[FIG. 8]
Figure 9:
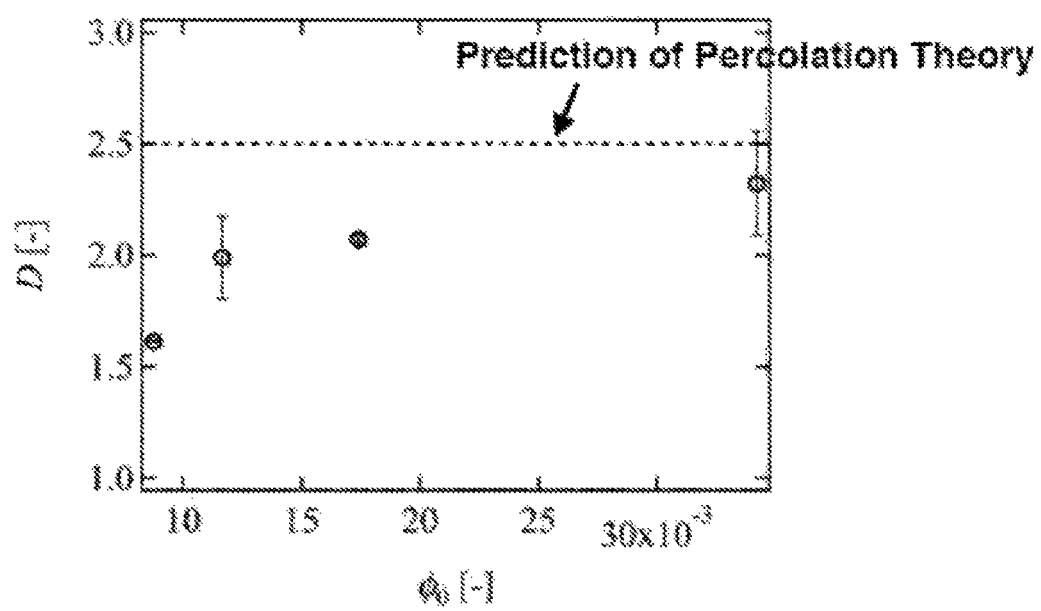
[FIG. 9]

FIG. 8 shows the results obtained b measuring the dynamic viscosity characteristics at the gelation critical point when various starting concentrations of polymer units were used. In FIG. 8, the vertical axis is the storage modulus G' (○ in the graph) and loss modulus G" (Δ in the graph), and the horizontal axis is the frequency. (a)-(d) are each starting concentration conditions. As shown in FIG. 8, the lower the staring concentration, the more the power law of G' and G" increased. The fractal dimension of the gel precursor clusters was calculated by dynamic scaling theory using this result. The results are shown in FIG. 9. In FIG. 9, the vertical axis if the fractal dimension, and the horizontal axis is the starting concentration. This graph suggested that the lower the concentration becomes, the more the fractal dimension D diverges downward from the theoretically predicted value (dotted line in the graph), forming a sparser structure.

Example 5

Properties of Polymer Gels

Figure 10:
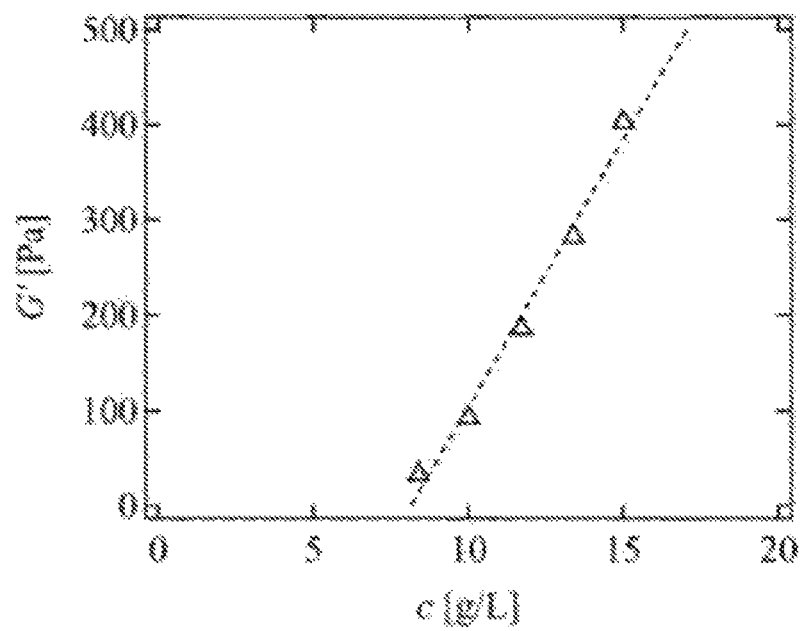
[FIG. 10]

The polymer concentration dependence of the modulus of elasticity of the polymer gel 1 obtained in Example 3 was also measured. As a result, as shown in FIG. 10, the modulus of elasticity was proportionate to the polymer content in the low concentration region of 20 g/L and the low modulus region where the storage modulus G' is less than 400 Pa. This proves that the modulus of elasticity of the gel can be controlled even in the low modulus of elasticity region by using a method of inducing gelation from gel precursor clusters.

Figure 11:
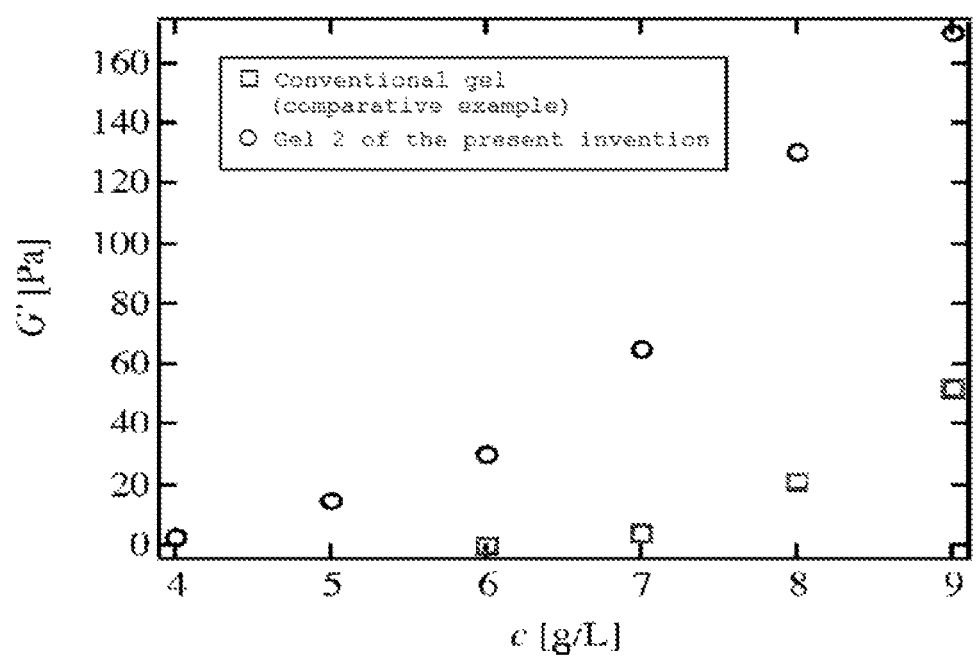
[FIG. 11]

Similarly, the polymer concentration dependence of the modulus of elasticity of the polymer gel 2 obtained in Example 3 was measured. The results are shown in FIG. 11. In the graph, ○ is an example of polymer gel of the present invention gelled by gel precursor clusters; □ is a comparative example gelled directly from polymer units by a conventional method without using gel precursor cluster. In all cases, the polymer gel of the present invention presented a higher modulus of elasticity, suggesting the formation of an effectively three-dimensional network structure.

Figure 12:
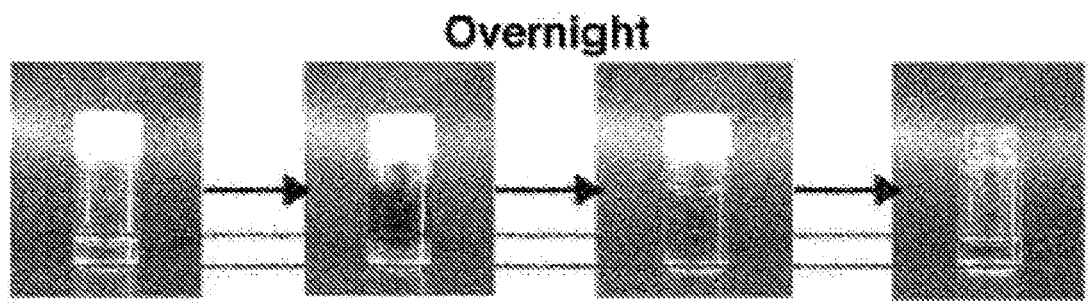
[FIG. 12]

The changes over time in expansion of the polymer gel 1 obtained in Example 3 were also observed in a pseudo semi-closed space. The polymer gel was placed in a glass container, phosphate buffer was added, and the container was allowed to stand overnight. As a result, as shown in FIG. 12, no changes in volume were demonstrated even in solution. This result suggests that the polymer gel is non-expansive in a semi-closed space and can be applied to closed spaced and semi-closed spaces in vivo.

Figure 13:
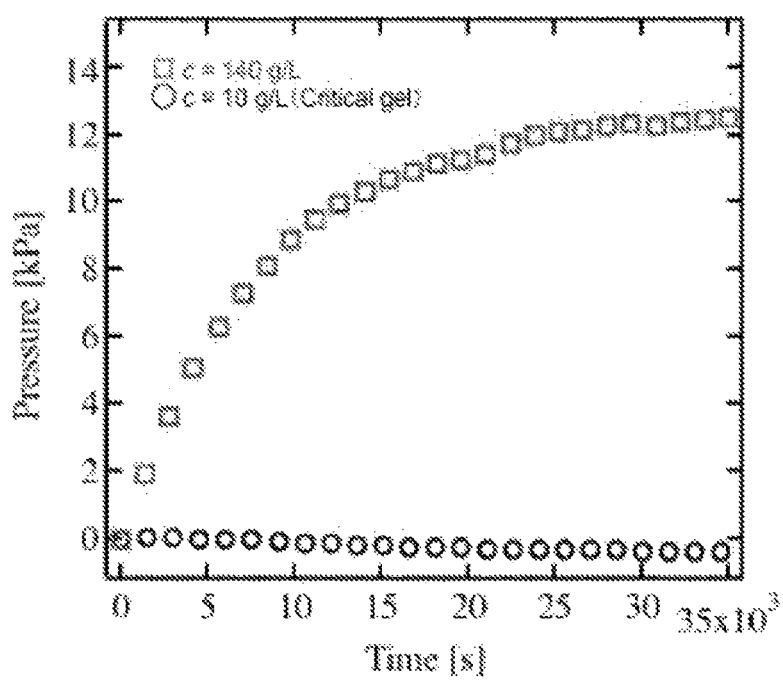
[FIG. 13]

Furthermore, FIG. 13 shows the results obtained by measuring the changes over time in the expansion pressure of polymer gel 2 obtained in Example 3. In the graph, ○ is an example (polymer concentration 10 g/L) of a polymer gel of the present invention gelled by gel precursor clusters; □ is a comparative example (polymer concentration 140 g/L) gelled directly from polymer units by a conventional method without using gel precursor clusters. As shown in FIG. 13, an equilibrium of 12 kPa is reached with the passage of time in the comparative example, but the polymer gel of the present invention was always constant at about 0.19 kPa. This result shows that the polymer gel of the present invention can be used over an extended period of time even when applied in vivo and a long time has elapsed.

Example 6

Versatility of Gel Precursor Clusters

The versatility of the gel precursor clusters was studied by producing low-concentration gels by the same procedure as the four-armed system in various systems.

[Three-Armed System]

Tri-APEG (triamine-polyethylene glycol) and Tri-NPEG (tri-N-hydroxysuccinimidyl-polyethylene glycol (NHS-PEG)), both having a molecular weight of $2.0 \times 10^5$, were dissolved in the same amounts of 45 mM phosphate buffer and citrate-phosphate buffer, respectively. The substance ratio at this time was Tri-APEG/Tri-NPEG=1/0.49, and the overall polymer concentration was set at 40 g/L. The two overall polymer concentration was set at 40 g/L. The two solutions obtained were mixed in a separate container, and defoamed and stirred with a planetary centrifugal mixer. The mixed solution was then transferred quickly to a Falcon tube, capped to prevent drying, and allowed to stand for 12 hours at room temperature. The solution obtained was diluted by water to make 25 g/L. The amount of unreacted amino groups in the solution was calculated, a crosslinking agent (bis(sulfosuccinimidyl) glutarate ($BS_2G$) was added in an amount equal thereto, and the system was defoamed and stirred with a planetary centrifugal mixer. The mixed solution was then quickly transferred to a Falcon tube, capped to prevent drying, and allowed to stand for 12 hours at room temperature. A gel was finally obtained in the same way as n the four-armed system.

[Four-Armed System/Two-Armed System]

Tri-APEG (triamine-polyethylene glycol) and linear-NPEG (linear-N-hydroxysuccinimidyl-polyethylene glycol (NHS-PEG)), having a molecular weight of $2.0 \times 10^5$ and $1.0 \times 10^5$, respectively, were each dissolved in the same amounts of 42 mM phosphate buffer and citrate-phosphate buffer, respectively. The substance ratio at this time was Tri-APEG/Tri-NPEG=1/1.17, and the overall polymer concentration was set at 40 g/L. The two solutions obtained were mixed in a separate container, and defoamed and stirred with a planetary centrifugal mixer. The mixed solution was then transferred quickly to a Falcon tube, capped to prevent drying, and allowed to stand for 12 hours at room temperature. The solution obtained was diluted by water to make 25 g/L. The amount of unreacted amino groups in the solution was calculated, a crosslinking agent (bis(sulfosuccinimidyl) glutarate ($BS_2G$)) was added in an amount equal thereto, and the system was defoamed and stirred with a planetary centrifugal mixer. The mixed solution was then quickly transferred to a Falcon tube, capped to prevent drying, and allowed to stand for 12 hours at room temperature. A gel was finally obtained in the same way as in the four-armed system.

The gel precursor clusters were understood to be highly versatile because gels were obtained by the same procedure as in the four-armed system even in a three-armed system and a four-armed/two-armed system.

Example 7

Injection Experiment into Mice

The polymer gel of the present invention was injected into mice by the following procedure.

1. Preparation of Gel Precursor Clusters

Tetra-PEG-maleimide (TMPEG) ($1.0 \times 10^4$ g/mol) and tetra-PEG-thiol (TTPEG) ($1.0 \times 10^4$) g/mol) were weighed out to make the substance ratios shown in the table below, and each was dissolve dins the same amount of citrate-phosphate buffer (pH 5.8, 5 mM (NaCl, 149 mM)). The overall polymer concentration at this time was set at 60 g/L. The two solutions obtained were mixed in a Falcon tube, capped to prevent drying, and allowed to stand for 12 hours at room temperature.

TABLE 1

| | Substance ratio (TMPEG:TTPEG) | Polymer concentration (g/L) |
| --- | --- | --- |
| Group 1 | 1:0.15 | 60 |
| Group 2 | 0.16:1 | 60 |

2. Preparation of Polymer Gel

Gel precursor cluster solutions were weighed out so that the total amount of polymer gel was 2 mL and the respective polymer concentrations were 13 g/L (group 1) and 11 g/L (group 2), and placed in syringes. The amounts of unreacted maleimide groups and thiol groups were also calculated in groups 1 and 2, respectively, and crosslinking agents (DL-dithiothreitol and 1,8-bismaleimidodiethyleneglycol) were each weighted out to make an amount equal thereto. The crosslinking agent was dissolved in citrate-phosphate buffer (pH 5.9, 5 mM (NaCl, 149 mM) of the total amount of polymer gel and the difference amount of gel precursor clusters, respectively, and placed in syringes separate form the above syringes. The two solutions were mixed using a three-way valve, and 1 mL was injected into the back of an anesthetized mouse. TMPEG alone (monomer A) and TTPEG alone (monomer B) dissolved in citrate-phosphate buffer (pH 5.8, 5 mM (NaCl, 149 mM) to make 15 g/L and citrate-phosphate buffer (pH 5.8, 5 mM (NaCl, 149 mM)) alone (control sample) were used as comparative examples, and 1 mL of each was injected into the backs of anesthetized mice. The tissues of the mouse were observed one week after injection.

As a result, no degradation of the gel or rejection reaction was seen in groups 1 or 2, and the presence of the gel under the skin was recognized even one week after injection. On the other hand, the monomers degraded without any toxic effects when injected alone. All of the mice were normal, with no changes in weight.

The invention claimed is:

1. A process for producing a polymer gel that forms a three-dimensional network structure by crosslinking of gel precursor clusters with one another, wherein the process comprises:

a) a step in which monomer units or polymer units that are present in a concentration less than a critical gelation concentration are crosslinked to form the gel precursor clusters, the gel precursor clusters having a storage modulus G' and a loss modulus G" which satisfy the relationship G'<G"; and b) a step in which the gel precursor clusters are crosslinked with one another with a crosslinking agent to obtain a gel having a three-dimensional network structure, wherein the gel has a polymer content of 50 g/L or less.

2. The process according to claim 1 wherein the loss modulus G" is in a range of 0.005-5 Pa at a frequency of 1 Hz.

3. The process according to claim 1 or 2 wherein the gel precursor clusters have a fractal dimension of 1.5-2.5.

4. The process according to claim 1, wherein the gel precursor clusters have a diameter in a range of 10-1000 nm.

5. The process according to claim 1, wherein the monomer unit has a vinyl skeleton or the polymer unit has a polyethylene glycol skeleton or a polyvinyl skeleton.

6. The process according to claim 1, wherein the gel precursor clusters comprise a first polymer unit having one or more nucleophilic functional groups in a side chain or at an end and a second polymer unit having one or more electrophilic functional groups in a side chain or at an end.

7. The process according to claim 6 wherein the nucleophilic functional groups are selected from the group consisting of an amino group, —SH, and —$CO_2PhNO_2$, and the electrophilic functional groups are selected from the group consisting of an N-hydroxysuccinimidyl (NHS) group, sulfosuccinimidyl group, maleimidyl group, phthalimidyl group, imidazoyl group, acryloyl group, and nitrophenyl group.

8. The process according to claim 6 or 7 wherein the gel precursor clusters comprise first gel precursor clusters and second gel precursor clusters, the first gel precursor clusters having a higher first polymer unit content than second polymer unit content, and the second gel precursor clusters having a higher second polymer unit content than first polymer unit content.

9. The process according to claim 1, wherein step b) is conducted with a reaction time of within one hour.

10. The process according to claim 1, wherein the crosslinking agent in step b) is bis(sulfosuccinimidyl) glutarate ($BS_2G$), DL-dithiothreitol (DTT), or a synthetic peptide having a thiol group at an end.

11. Gel precursor clusters obtained by crosslinking monomer units or polymer units present in a concentration less than a critical gelation concentration wherein the gel precursor clusters contain a solvent
and have a storage modulus G' and a loss modulus G" in a relationship of G'<G", and wherein the gel precursor clusters have a diameter in a range of 10-1000 nm.

12. Gel precursor clusters according to claim 11 wherein the loss modulus G" is in a range of 0.005-5 Pa at a frequency of 1 Hz.

13. Gel precursor clusters according to claim 11 or 12 wherein the gel precursor clusters have a fractal dimension of 1.5-2.5.

14. Gel precursor clusters according to claim 11, wherein the monomer unit has a vinyl skeleton or the polymer unit has a polyethylene glycol skeleton or a polyvinyl skeleton.

15. Gel precursor clusters according to claim 11, comprising a first polymer unit having one or more nucleophilic functional groups in a side chain or at an end and a second polymer unit having one or more electrophilic functional groups in a side chain or at an end.

16. Gel precursor clusters according to claim 15 wherein the nucleophilic functional groups are selected from the group consisting of an amino group, —SH, and —CO$_2$PhNO$_2$, and the electrophilic functional groups are selected from the group consisting of an N-hydroxysuccinimidyl (NHS) group, sulfosuccinimidyl group, maleimidyl group, phthalimidyl group, imidazoyl group, acryloyl group, and nitrophenyl group.

17. A polymer gel obtained by the process according to claim 1.

18. A polymer gel that forms a three-dimensional network structure by crosslinking polymer units with each other wherein the polymer gel
contains a solvent,
has a polymer content of 50 g/L or less,
has a storage modulus G' of 1-10,000 Pa at a frequency of 1 Hz, and
has a fractal dimension of 1.5-3.0,
wherein the degree of expansion is such that the change in the volume of the polymer gel in a range of 30-40° C. in an aqueous solution is 90-500% relative to the volume at the time of gel production and the expansion pressure is 0.001-5 kPa.

19. The polymer gel according to claim 18 having a loss modulus G" of 1-100 Pa.

20. The polymer gel according to claim 18 or 19 wherein the monomer unit has a vinyl skeleton or the polymer unit has a polyethylene glycol skeleton or polyvinyl skeleton.

21. The polymer gel according to claim 18, wherein the polymer units comprise a first polymer unit having one or more nucleophilic functional groups in a side chain or at an end and a second polymer unit having one or more electrophilic functional groups in a side chain or at an end.

22. The polymer gel according to claim 21 wherein the nucleophilic functional groups are selected from the group consisting of an amino group, —SH, and —CO$_2$PhNO$_2$, and the electrophilic functional groups are selected from the group consisting of an N-hydroxysuccinimidyl (NHS) group, sulfosuccinimidyl group, maleimidyl group, phthalimidyl group, imidazoyl group, acryloyl group, and nitrophenyl group.

23. The polymer gel according to claim 20 wherein the degree of expansion is in a range of 100-200% and the expansion pressure is 0.1-2 kPa.

* * * * *